US006288127B1

(12) United States Patent
Bieniarz et al.

(10) Patent No.: US 6,288,127 B1
(45) Date of Patent: *Sep. 11, 2001

(54) FLUOROETHER COMPOSITIONS AND METHODS FOR INHIBITING THEIR DEGRADATION IN THE PRESENCE OF A LEWIS ACID

(75) Inventors: Christopher Bieniarz, Highland Park; Steve H. Chang, Gurnee; Keith R. Cromack, Lake Bluff; Shuyen L. Huang, Riverwoods, all of IL (US); Toshikazu Kawai; Manami Kobayashi, both of Saitama (JP); David Loffredo, Elmhurst, IL (US); Rajagopalan Raghavan, Grayslake, IL (US); Earl R. Speicher, Buffalo Grove, IL (US); Honorate A. Stelmach, Lake Forest, IL (US)

(73) Assignee: Abbott Laboratories & Central Glass Co LTD, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/447,853

(22) Filed: Nov. 23, 1999

Related U.S. Application Data (63) Continuation of application No. 08/789,679, filed on Jan. 27, 1997, now Pat. No. 5,990,176.

(51) Int. Cl.$^7$ .............................. A61K 31/08; C07C 43/12
(52) U.S. Cl. ..................... 514/722; 568/683; 568/684; 514/816
(58) Field of Search ..................... 514/722, 816; 568/683, 684

(56) References Cited

U.S. PATENT DOCUMENTS

| 2,992,276 | 7/1961 | Weinmayr | 260/614 |
|---|---|---|---|
| 3,527,813 | 9/1970 | Terrell | 260/614 |
| 3,689,571 | 9/1972 | Regan et al. | 260/614 |
| 4,080,389 | * 3/1978 | Moilliet | 260/614 |
| 4,250,334 | 2/1981 | Coon et al. | 568/683 |
| 4,469,898 | 9/1984 | Coon et al. | 568/683 |
| 5,684,211 | 11/1997 | Kawai et al. | 568/682 |
| 5,990,176 | * 11/1999 | Bieniarz et al. | 514/722 |

OTHER PUBLICATIONS

USP XXII, Official Monograph, p. 726 (isoflurane).
A. Carre, F. Roger, and C. Varinot, "Study of Acid/Base Properties of Oxide Glass, and Glass–Ceramics Surfaces," *Journal of Colloid and Interface Science,* vol. 154, No. 1, Nov. 1972.
M. Hair, "The Nature of Leached Glass Surface," *Clean Surfaces: Their Preparation and Characterization for Interfacial Studies,* Published by Marcel Dekker, Inc. (New York) 1970.
I. Chistovskaya and F. Janowski, "Acidic and Catalytic Properties of Boron –Containing Porous Glasses," *React.Kinet.Catal. Lett.,* vol. 43, No. 2, 277–282 (1991).
J.Jednacak–Biscan, V. Pravdic, and W. Haller, "Adsorption Phenomena on Glass Surfaces," *Journal of Colloid and Interface Science,* vol. 121, No. 2, Feb. 1988.
J. March, "Advanced Organic Chemistry," McGraw–Hill Book Company (New York).
XP–002061443; "The Dedgradation, Absorption and Solubility of Volatile Anesthetics in Soda Lime Depend on Water Content": David P. Strum, MD, FRCP, and Edmond I. Eger II, MD; vol. 78, No.2; Feb. 1994; Baltimore; pp. 340–348.
Smith, I. et al., Comparison of Induction, Mainteance, and Recovery Characteristics of Sevoflurane ——N$_2$O Anesthesia. Anes. Analg. vol. 74, pp. 253–259, 1992.
Sevoflurance Water Content, Abbott Laboratories.
XP–002061444; Dressing J., Spencer A., Kieviet O.S.: "Repertorium 94/95", 1994, NL., S–Gravenhage, SDU, The Hague.

\* cited by examiner

Primary Examiner—Charanjit S. Aulakh
(74) Attorney, Agent, or Firm—Brian R. Woodworth (57) ABSTRACT

The present invention relates to an anesthetic composition containing a fluoroether compound and a physiologically acceptable Lewis acid inhibitor. This composition exhibits improved stability and does not readily degrade in the presence of a Lewis acid.

10 Claims, 5 Drawing Sheets

FLUOROETHER COMPOSITIONS AND METHODS FOR INHIBITING THEIR DEGRADATION IN THE PRESENCE OF A LEWIS ACID

This application is a continuation of U.S. Ser. No. 08/789,679 filed Jan. 27, 1997, now U.S. Pat. No. 5,990,176.

TECHNICAL FIELD OF THE INVENTION

The present invention relates generally to stable, anesthetic fluoroether compositions that do not degrade in the presence of a Lewis acid. The present invention also relates to a method of inhibiting the degradation of fluoroethers in the presence of Lewis acids.

BACKGROUND OF THE INVENTION

Fluoroether compounds are commonly employed as anesthetic agents. Examples of fluoroether compounds used as anesthetic agents include sevoflurane (fluoromethyl-2,2,2-trifluoro-1-(trifluoromethyl)ethyl ether), enflurane ((±)-2-chloro-1,1,2-trifluoroethyl difluoromethyl ether), isoflurane (1-chloro-2,2,2-trifluoroethyl difluoromethyl ether), methoxyflurane (2,2-dichloro-1,1-difluoroethyl methyl ether), and desflurane ((±)-2-difluoromethyl 1,2,2,2-tetrafluoroethyl ether).

Although fluoroethers are excellent anesthetic agents, it has been discovered that some fluoroethers experience stability problems. More specifically, it has been determined that certain fluoroethers, in the presence of one or more Lewis acids, degrade into several products including potentially toxic chemicals such as hydrofluoric acid Hydrofluoric acid is toxic by ingestion and inhalation and is highly corrosive to skin and mucous membranes. Thereupon, the degradation of fluoroethers to chemicals such hydrofluoric acid is of great concern to the medical community.

Degradation of fluoroethers has been found to occur in glass containers. The degradation of fluoroethers in glass containers is believed to be activated by trace amounts of Lewis acids present in the container. The source of the Lewis acids can be aluminum oxides, which are a natural component of glass. When the glass wall becomes altered or etched in some manner, the aluminum oxide become exposed and come into contact with the contents of the container. The Lewis acids then attack the fluoroether and degrade it.

For example, when the fluoroether sevoflurane is contacted with one or more Lewis acids in a glass container under anhydrous conditions, the Lewis acid initiates the degradation of sevoflurane to hydrofluoric acid and several degradation products. The degradation products of sevoflurane are hexafluoroisopropyl alcohol, methyleneglycol bishexafluoroisopropyl ether, dimethyleneglycol bishexafluoroisopropyl ether and methyleneglycol fluoromethyl hexafluoroisopropyl ether. The hydrofluoric acid proceeds to further attack the glass surface and expose more of the Lewis acid on the glass surface. This results in further degradation of sevoflurane.

The degradation mechanism of sevoflurane in the presence of a Lewis acid can be illustrated as follows:

Therefore, a need exists in the art for a stable anesthetic composition containing fluoroether compounds that does not degrade in the presence of a Lewis acid.

SUMMARY OF THE INVENTION

The present invention involves a stable anesthetic composition that contains a fluoroether compound having an alpha fluoroether moiety having added thereto an effective stabilizing amount of a Lewis acid inhibitor. The preferred fluoroether compound is sevoflurane and the preferred Lewis acid inhibitor is water. The composition can be prepared by adding the Lewis acid inhibitor to the fluoroether compound, by adding the fluoroether compound to the Lewis acid inhibitor, or by washing a container with the Lewis acid inhibitor and then adding the fluoroether compound.

The present invention also involves a method for stabilizing a fluoroether compound having an alpha fluoroether moiety. The method involves adding an effective stabilizing amount of a Lewis acid inhibitor to the fluoroether compound to prevent the degradation of the fluoroether compound by a Lewis acid. The preferred fluoroether compound is sevoflurane and the preferred Lewis acid inhibitor is water.

DETAILED DESCRIPTION OF THE INVENTION

The present invention provides a stable, anesthetic composition that does not degrade in the presence of a Lewis acid. The present invention also relates to methods of preparing said anesthetic composition.

The anesthetic composition of the present invention contains at least one fluoroether compound. The fluoroether compound used in the composition corresponds to Formula I, below.

(I)

In Formula I, each $R_1$; $R_2$; $R_3$; $R_4$; and $R_5$ can independently be a hydrogen, halogen, an alkyl group having from 1 to 4 carbon atoms ($C_1$–$C_4$ alkyl), or a substituted alkyl having from 1 to 4 carbon atoms ($C_1$–$C_4$ substituted alkyl). In the preferred embodiment of Formula I, $R_1$ and $R_3$ are each the substituted alkyl $CF_3$ and $R_2$, $R_4$ and $R_5$ are each a hydrogen.

As used herein, the term "alkyl" refers to a straight or branched chain alkyl group derived from saturated hydrocarbons by the removal of one hydrogen atom. Examples of alkyl groups include methyl, ethyl, n-propyl, isopropyl, n-butyl, sec-butyl, iso-butyl, tert-butyl, and the like. As used herein, the term "substituted alkyl" refers to an alkyl group substituted by one or more groups such as halogen, amino, methoxy, difluoromethyl, trifluoromethyl, dichloromethyl, chlorofluoromethyl, etc. As used herein, the term "halogen" refers to one of the electronegative elements of group VIIA of the periodic table.

The fluoroether compounds having the Formula I contain the alpha fluoroether moiety —C—O—C—F—. Lewis acids attack this moiety which results in the degradation of the fluoroether to various degradation products and toxic chemicals.

Examples of fluoroether compounds of Formula I that can be used in the present invention are sevoflurane, enflurane, isoflurane, methoxyflurane and desflurane. The preferred fluoroether compound for use in the present invention is sevoflurane.

Methods for making the fluoroether compounds having Formula I are well known in the art and can be used in preparing the composition of the present invention. For example, sevoflurane can be prepared using the methods described in U.S. Pat. No. 3,689,571 and U.S. Pat. No. 2,992,276 herein incorporated by reference.

The composition of the present invention contains a total of from about 98% w/w top about 100% w/w of a fluoroether compound having the Formula I. Preferably, the composition contains at least 99.0% w/w of the fluoroether compound.

The anesthetic composition of the present invention also contains a physiologically acceptable Lewis acid inhibitor. As used herein, "Lewis acid inhibitor" refers to any compound that interacts with the empty orbital of a Lewis acid thereby blocking the potential reaction sites of the acid. Any physiologically acceptable Lewis acid inhibitor can be used in the composition of the present invention. Examples of Lewis acid inhibitors that can be used in the present invention include water, butylated hydroxytoluene (1,6-bis(1,1-dimethyl-ethyl)-4-methylphenol), methylparaben (4-hydroxybenzoic acid methyl ester), propylparaben (4-hydroxybenzoic acid propyl ester), propofol (2,6-diisopropyl phenol) and thymol (5-methyl-2-(1-methylethyl)phenol).

The composition of the present invention contains an effective stabilizing amount of a Lewis acid inhibitor. It is believed that the effective stabilizing amount of Lewis acid inhibitor that can be used in the composition is about 0.0150% w/w (water equivalent) to about the saturation level of the Lewis acid inhibitor in the fluoroether compound. As used herein, the term "saturation level" means the maximum solubility level of the Lewis acid inhibitor in the fluoroether compound. It will be appreciated that the saturation level may be temperature dependent. The saturation level also will depend on the particular fluoroether compound and the particular Lewis acid inhibitor being used in the composition. For example, when the fluoroether compound is sevoflurane and the Lewis acid inhibitor is water, the amount of water employed to stabilize the composition is believed to be from about 0.0150% w/w to about 0.14% w/w (saturation level). It should be noted, however, that once the composition is exposed to Lewis acids, the amount of Lewis acid inhibitor in the composition may decrease as the Lewis acid inhibitor reacts with the Lewis acid to prevent the unwanted degradative reaction of Lewis acid inhibitor with the composition.

The Lewis acid inhibitor preferred for use in the composition of the present invention is water. Purified or distilled water or a combination of both can be used. As stated earlier, the effective amount of water that can be added to the composition is believed to be about 0.0150% w/w to about 0.14% w/w, and is preferably about 0.0400% w/w to about 0.0800% w/w. For any other Lewis acid inhibitor, a molar equivalent based upon moles of water should be used.

When the fluoroether compound is exposed to a Lewis acid, the physiologically acceptable Lewis acid inhibitor present in the composition donates electrons to the empty orbital of the Lewis acid and forms a covalent bond between the inhibitor and the acid. Thereupon, the Lewis acid is prevented from reacting with the alpha fluoroether moiety of the fluoroether and degrading the fluoroether.

The composition of the present invention can be prepared in several ways. In one aspect, a container, such as a glass bottle, is first washed or rinsed with the Lewis acid inhibitor and then filled with the fluoroether compound. Optionally, the container may be partially dried after the washing or rinsing. Once the fluoroether is added to the container, the container is sealed. As used herein, the term "partially dried"

refers to an incomplete drying process that leaves a residual of a compound on or in the container being dried. Also as used herein, the term "container" refers to a receptacle made from glass, plastic, steel or other material that can be used for holding goods. Examples of containers include bottles, ampules, test tubes, beakers, etc.

In another aspect, the Lewis acid inhibitor is added to a dried container prior to filling the container with the fluoroether compound. Once the Lewis acid inhibitor has been added, the fluoroether compound is added to the container. Alternatively, the Lewis acid inhibitor may be added directly to a container already containing the fluoroether compound.

In another aspect, the Lewis acid inhibitor may be added to a container filled with the fluoroether compound under humid conditions. For example, water can be added to a container filled with the fluoroether compound by placing the container in a humidity chamber for a sufficient amount of time to allow the water to accumulate in the container.

The Lewis acid inhibitor can be added to the composition at any appropriate point in the manufacturing process, e.g., at the final manufacturing step before filling into shipping containers, e.g., 500 liter shipping container. Appropriate quantities of the composition can be dispensed from the container and packaged in containers of more suitable size for use in the industry, such as 250 mL glass bottles. Additionally, small quantities of the composition containing appropriate amounts of the Lewis acid inhibitor can be used to wash or rinse containers to neutralize any Lewis acids that might be present in the container. Once the Lewis acids have been neutralized, the container may be emptied and additional quantities of the fluoroether composition added to the container prior to sealing the container.

By way of example, but not of limitation, examples of the present invention will now be given.

EXAMPLE 1

Activated Alumina as a Lewis Acid

Type III glass consists mainly of silicon dioxide, calcium oxide, sodium oxide and aluminum oxide. Aluminum oxide is a known Lewis acid. The glass matrix is normally inert to sevoflurane. However, under certain conditions (anhydrous, acidic), the glass surface can be attacked or altered, exposing sevoflurane to active Lewis acid sites such as aluminum oxide.

The effect of water on the degradation of sevoflurane was studied by adding various amounts of activated alumina to 20 ml of sevoflurane containing the following three levels of moisture: 1) 20 ppm water—measured water, no additional water added; 2) 100 ppm—spiked; and 3) 260 ppm water—spiked. Table 1 below shows the experimental matrix.

TABLE 1

| | 1 | 2 | 3 |
|---|---|---|---|
| A | 50 mg $Al_2O_3$ 20 ppm Water | 50 mg $Al_2O_3$ 100 ppm Water | 50 mg $Al_2O_3$ 260 ppm Water |
| B | 20 mg $Al_2O_3$ 20 ppm Water | 20 mg $Al_2O_3$ 100 ppm Water | 20 mg $Al_2O_3$ 260 ppm Water |
| C | 10 mg $Al_2O_3$ 20 ppm Water | 10 mg $Al_2O_3$ 100 ppm Water | 10 mg $Al_2O_3$ 260 ppm Water |

Figure 1:
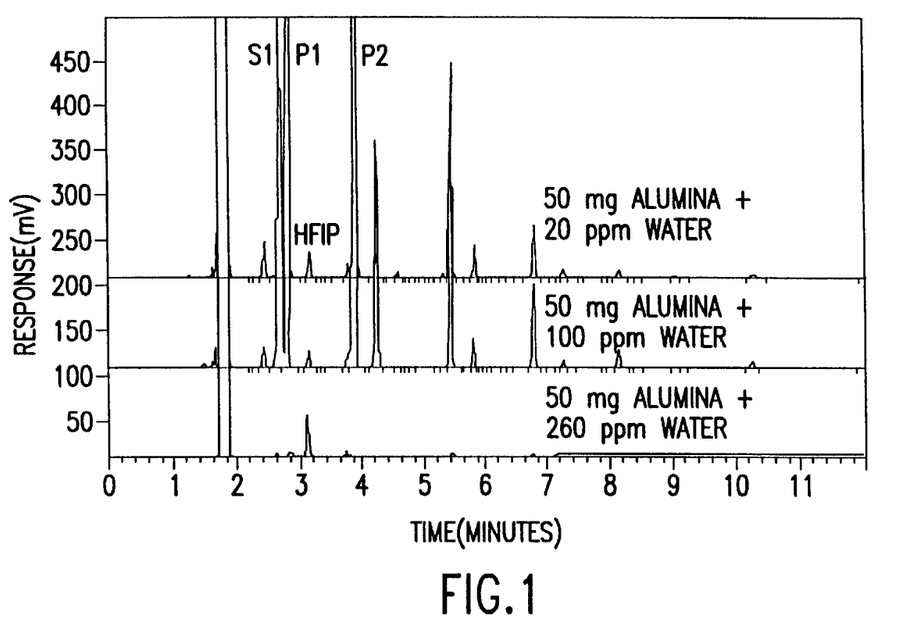
FIG. 1 shows a chromatogram demonstrating that in the presence of the same amount of aluminum oxide (50 mg), the degradation of sevoflurane decreases with increasing amounts of water. The identified degradation products of sevoflurane shown in FIG. 1 are hexafluoroisopropyl alcohol (HFIP), methyleneglycol bishexafluoroisopropyl ether (P1), dimethyleneglycol bishexafluoroisopropyl ether (P2) and methyleneglycol fluoromethyl hexafluoroisopropyl ether (S1).

It will be appreciated that 20 ppm Water is equivalent to 0.0022% w/w Water. The samples were placed at 60° C. and analyzed by gas chromatography after 22 hours. FIG. 1 shows that in the presence of the same amount of aluminum oxide (50 mg) that the degradation of sevoflurane decreases with increasing amounts of water (Row A from Table 1). A similar trend was observed for 20 mg and 10 mg of aluminum oxide (Rows B and C).

EXAMPLE 2

Figure 2:
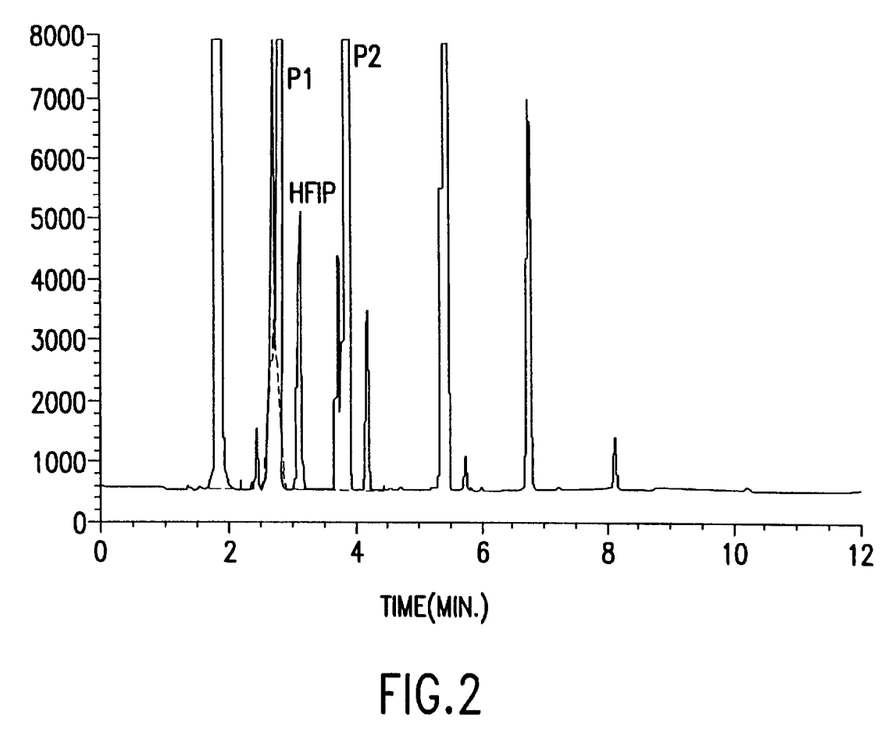
FIG. 2 depicts a chromatogram showing the degradation of sevoflurane after heating in an autoclave at 119° C. for 3 hours.
Figure 3:
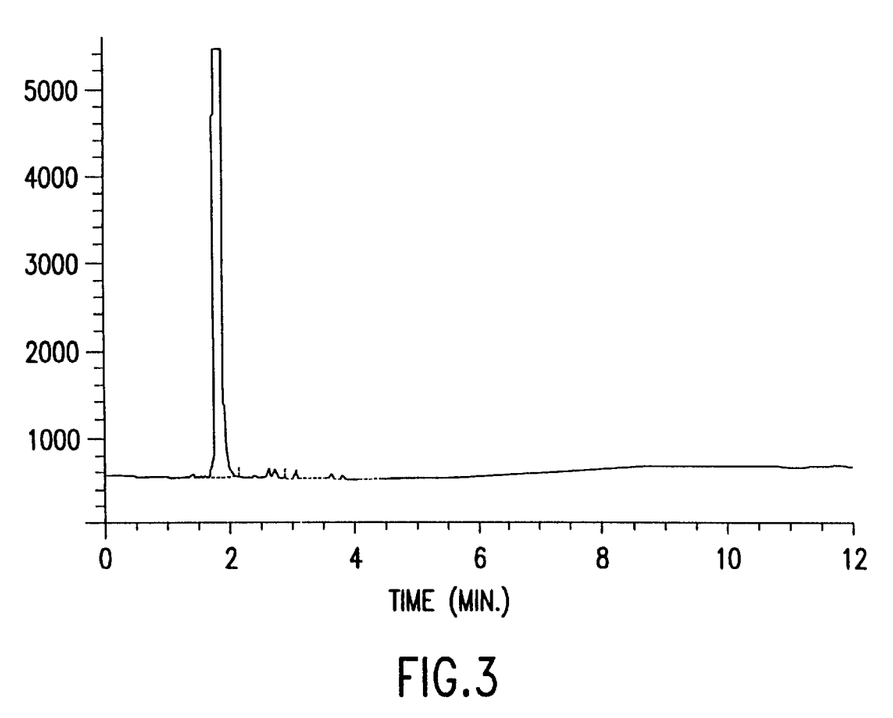
FIG. 3 depicts a chromatogram showing the effects of water on the inhibition of the degradation of sevoflurane after heating in an autoclave at 119° C. for 3 hours.

Degradation in Ampules of Sevoflurane by Heat With and Without the Addition of Water Approximately 20 mL of sevoflurane was added to a 50 mL Type I clear ampule and approximately 20 mL of sevoflurane and 1300 ppm of water was added to a second ampule. Both ampules were flame-sealed and then autoclaved at 119° C. for three hours. The contents of the two ampules were then analyzed by gas chromatography. FIG. 2 shows that the sevoflurane in the first ampule degraded. FIG. 3 shows that the sevoflurane in the second ampule did not degrade as a result of the Lewis acid inhibitor, namely the added water.

EXAMPLE 3

Degradation of Sevoflurane in Ampules Using Water-Spiked Studies (109 ppm to 951 ppm)

Type I clear glass ampules were used to study the effect of various levels of water in inhibiting the degradation of sevoflurane. Approximately 20 mL of sevoflurane and different levels of water ranging from about 109 ppm to about 951 ppm were added to each ampule. The ampules were then sealed. A total of ten ampules were filled with sevoflurane and varying amounts of water. Five of the ampules were included in Set A and the other five ampules were included in Set B. The ampules were then autoclaved at 119° C. for three hours. Samples in Set A were placed on a mechanical shaker overnight to allow the moisture to coat the glass surface. Samples in Set B were prepared without equilibrating the water with the glass surface. Several control samples were also prepared. Two non-autoclaved ampules (Control Ampule 1 and Control Ampule 2) and a bottle (Control bottle) were each filled with 20 mL of sevoflurane. No water was added to any of the control samples. Also, the controls samples were not shaken overnight. The levels of hexafluoroisopropanol (HFIP) and total degradants (including methyleneglycol bishexafluoroisopropyl ether, dimethyleneglycol bishexafluoroisopropyl ether, methyleneglycol fluoromethyl hexafluoro isopropyl ether) were measured by gas chromatography. The results are shown below in Table 2.

TABLE 2

| Sample | Total Moisture Calculated (ppm) | pH | HFIP (ppm) | Total Degradants without HFIP (ppm) |
|---|---|---|---|---|
| Control, Bottle | | 6.0 | 6 | 57 |
| Control, Ampule 1, RT | | 3.0 | 7 | 50 |
| Control, Ampule 2, RT | | 4.0 | 6 | 51 |
| Set A (Shaken Overnight) | | | | |
| 1 | 109 | 0 | 1,525 | 201614 |
| 2 | 206 | 0 | 2,456 | 105518 |
| 3 | 303 | 0 | 4,027 | 127134 |
| 4 | 595 | 5.0 | 7 | 82 |
| 5 | 951 | 5.0 | 12 | 84 |

TABLE 2-continued

| Sample | Total Moisture Calculated (ppm) | pH | HFIP (ppm) | Total Degradants without HFIP (ppm) |
|---|---|---|---|---|
| Set B (Not Shaken) | | | | |
| 1 | 109 | 0 | 1,936 | 195364 |
| 2 | 206 | 0 | 3,390 | 170869 |
| 3 | 303 | 0 | 5,269 | 101845 |
| 4 | 595 | 6.0 | 21 | 107 |
| 5 | 951 | 6.0 | 10 | 63 |

The results in Table 2 above demonstrate that for the ampules in Set A and in Set B, at least 595 ppm of water was sufficient to inhibit the degradation of sevoflurane. The results show no significant difference between the ampules that were shaken overnight and those that were not shaken overnight.

EXAMPLE 4

Degradation of Sevoflurane in Ampules Using Water Spiked Sevoflurane Studies at 60° C. or 40° C.

Type I clear glass ampules were employed to study the effect of various levels of water and temperature in inhibiting the degradation of sevoflurane. Approximately 20 mL of sevoflurane and different levels of water ranging from about 109 ppm to about 951 ppm were added to each ampule. The ampules were then flame-sealed. To accelerate the degradation process, samples from each moisture level were placed at two heating conditions. Samples were placed on a 60° C. stability station for 144 hours or placed on a 40° C. stability station for 200 hours. The resulting sevoflurane in each of the samples was analyzed by gas chromatography and pH. Hexafluoroisopropyl alcohol (HFIP) and the total degradants of sevoflurane were measured. The results are shown below in Table 3.

TABLE 3

| Sample | Total Moisture | pH | HFIP (ppm) | Total Degradants (ppm) |
|---|---|---|---|---|
| Water-spiked, 60° C., 144 hrs | | | | |
| 1 | 109 | 0 | 850 | 474796 |
| 2 | 206 | 3.5 | 7 | 48 |
|   |     |     | 8 | 65 |
| 3-1 | 303 | 3.5 | 13 | 68 |
|   |     |     | 16 | 88 |
| 3-2 | 303 | 5.0 | 8 | 60 |
| 4 | 595 | 5.5 | 7 | 66 |
| 5-1 | 951 | 5.5 | 4 | 52 |
| 5-2 | 951 | 5.5 | 5 | 60 |
| Water-spiked, 40° C., 200 hrs | | | | |
| 6-1 | No H$_2$O added | 0 | 232 | 102435 |
| 6-2 | No H$_2$O added | 2.5 | 24 | 68 |
| 7 | 109 | 3.0 | 40 | 77 |
| 8 | 206 | 5.0 | 7 | 59 |
| 9 | 303 | 5.0 | 6 | 59 |
| 10 | 595 | 6.0 | 6 | 60 |
| 11 | 951 | 6.0 | 5 | 60 |

The results in Table 3 demonstrate that at 40° C. for 200 hours, water levels higher than 206 ppm inhibit the degradation of sevoflurane. For samples stored at 60° C. for 144 hours or longer, water levels higher than 303 ppm inhibit the degradation of sevoflurane. This data suggests that as the temperature increases, the amount of water required to inhibit the degradation of sevoflurane will increase.

EXAMPLE 5

Sevoflurane Degradation in Activated Type III Amber Glass Bottles

Type III amber glass bottles that were used to store degraded sevoflurane were examined. Those bottles that exhibited a significant amount of etching inside the bottle were selected. A total of ten Type III amber glass bottles were selected. The degraded sevoflurane contained in each of these bottles was drained and the bottles were rinsed several times with non-degraded fresh sevoflurane. Approximately 100 mL of non-degraded sevoflurane containing about 20 ppm water was added to each bottle. Gas chromatography analysis for all the samples was performed at the time zero and after heating at 50° C. for 18 hours. Hexafluoroisopropyl alcohol (HFIP) and dimethyleneglycol ether (P2) were measured. The results are shown in Tables 4 and 5 below.

TABLE 4

Results at Time Zero

| | Degradation Products (ppm) | | |
|---|---|---|---|
| Bottle Number | HFIP | P2 | Total |
| 1 | 124 | <10 | 185 |
| 2 | 84 | <10 | 123 |
| 3 | 77 | <10 | 137 |
| 4 | 56 | <10 | 89 |
| 5 | 144 | <10 | 190 |
| 6 | 63 | <10 | 96 |
| 7 | 58 | <10 | 95 |
| 8 | 60 | <10 | 102 |
| 9 | 51 | <10 | 106 |
| 10 | 65 | <10 | 140 |

TABLE 5

Results at 50° C., 18 Hours

| | Degradation Products (ppm) | | |
|---|---|---|---|
| Bottle Number | HFIP | P2 | Total |
| 1 | 1026 | 7938 | 14243 |
| 2 | 912 | 3013 | 6428 |
| 3 | 1160 | 4662 | 10474 |
| 4 | 908 | 3117 | 7381 |
| 5 | 907 | 6687 | 11774 |
| 6 | 1128 | 5448 | 11313 |
| 7 | 1152 | 2371 | 6695 |
| 8 | 1199 | 2925 | 7386 |
| 9 | 1560 | 4183 | 10325 |
| 10 | 1455 | 2255 | 6667 |

The results in Tables 4 and 5 show that the glass surfaces in these bottles were "activated" by degraded sevoflurane. "Activated" glass surfaces thus served as initiators for the degradation of fresh sevoflurane.

EXAMPLE 6

Additional Studies of Sevoflurane Degradation In Activated Type III Amber Glass Bottles The extent of the degradation of sevoflurane in each of the bottles from Example 5 were quantified by gas chromatography. The ten bottles were divided into two groups, the Control Sevo Group (containing bottles 2, 3, 5, 7, 8) and the Study Sevo Group (containing Bottles 1, 4, 6, 9, 10).

All ten bottles were re-rinsed several times with non-degraded sevoflurane containing about 20 ppm of water. For the five Control Sevo Group bottles, 100 mL of sevoflurane containing about 20 ppm of water was added to each bottle. For the five Study Group bottles, 100 mL of sevoflurane containing about 400 ppm of water (spiked) was added to each bottle.

Gas chromatography for all samples was performed at time zero and after heating at 50° C. for 18 hours. Hexafluoroisopropyl alcohol (HFIP), dimethyleneglycol bishexafluoroisopropyl ether (P2) and total degradants were measured. The results are shown below in Table 6.

TABLE 6

Results at the Zero Hour and Eighteen Hours

| | Degradation Products (ppm) | | | | | |
|---|---|---|---|---|---|---|
| | HFIP | | P2 | | Total | |
| Time | 0 hour | 18 hour | 0 hour | 18 hour | 0 hour | 18 hour |
| Control Group (20 ppm water) | | | | | | |
| 2 | <10 | 777 | <10 | 2291 | <50 | 5995 |
| 3 | <10 | 790 | <10 | 2714 | <50 | 6552 |
| 5 | 11 | 688 | <10 | 2446 | <50 | 5485 |
| 7 | <10 | 894 | <10 | 1171 | <50 | 4124 |
| 8 | <10 | 824 | <10 | 1950 | <50 | 5139 |
| Study Group (400 ppm water) | | | | | | |
| 1 | 12 | 605 | <10 | <10 | <50 | 669 |
| 4 | <10 | 84 | <10 | <10 | <50 | 98 |
| 6 | <10 | 331 | <10 | <10 | <50 | 357 |
| 9 | <10 | 294 | <10 | <10 | <50 | 315 |
| 10 | 10 | 528 | <10 | <10 | <50 | 577 |

The results in Table 6 show that at zero hour, no significant degradation of sevoflurane was observed when compared to that of the zero-hour results in Table 4. The results in Table 6 show that, in the Study Sevo Group (400 ppm water), the degradation of sevoflurane was significantly reduced. The amounts of degradants P2 (dimethyleneglycol bishexafluoroisopropyl ether) and S1 (methyleneglycol fluoromethyl hexafluoroisopropyl ether) were much less than those in Control Group 1 (20 ppm water). The HFIP concentration in the Study Sevo Group, however, was quite high and suggests that the glass surfaces were still somewhat active.

Figure 4:
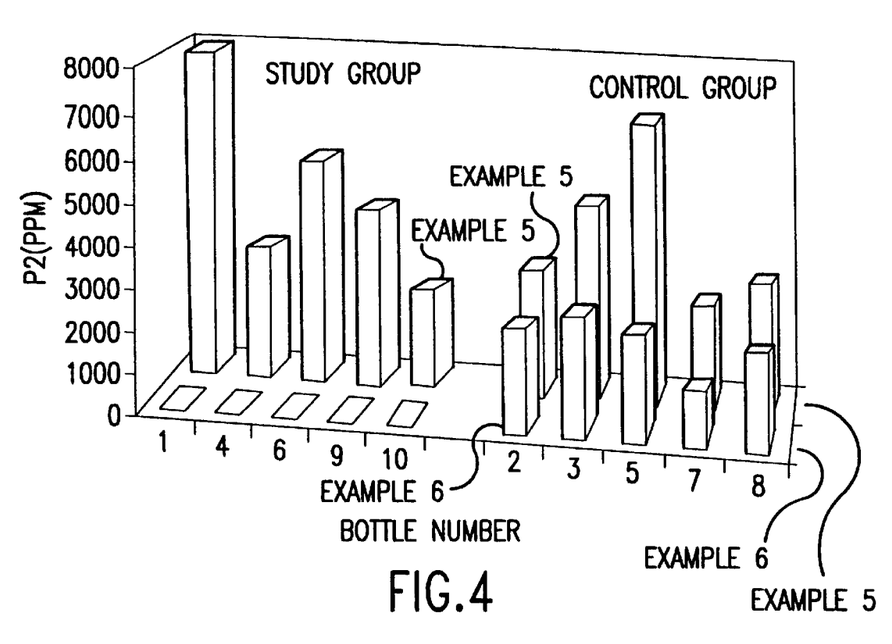
FIG. 4 shows a bar graph comparing the sevoflurane degradant P2 in activated type III amber glass bottles from Examples 5 and 6. The graph demonstrates that the degradation of sevoflurane is inhibited by the addition of 400 ppm of water.
Figure 5:
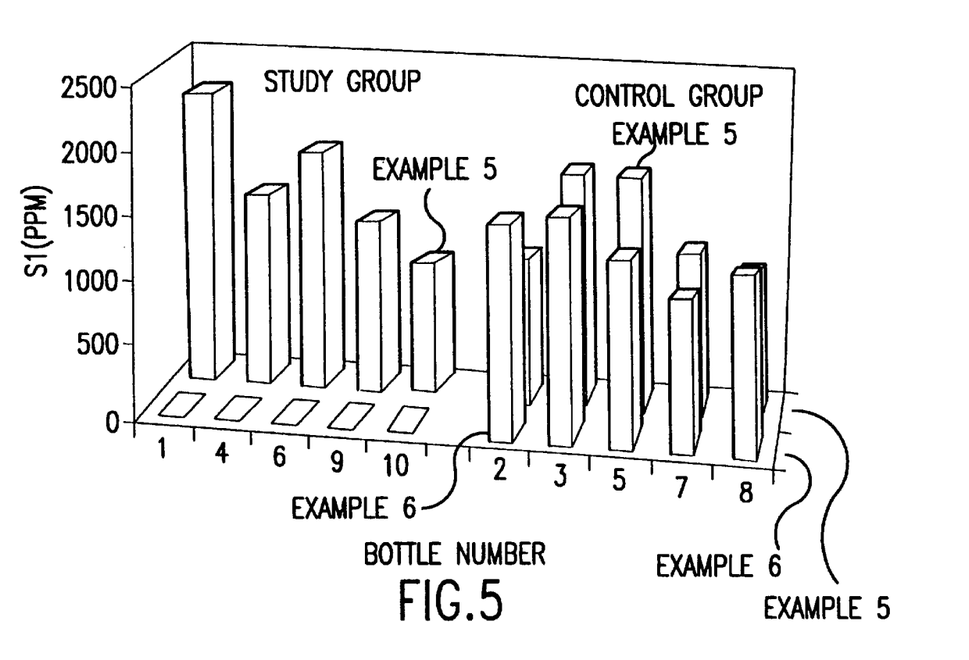
FIG. 5 shows a bar graph comparing the sevoflurane degradant S1 in activated type III amber glass bottles from Examples 5 and 6. The graph shows that the degradation of sevoflurane is inhibited by the addition of 400 ppm of water.

FIG. 4 shows a graphic comparison of the degradant dimethyleneglycol bishexafluoroisopropyl ether (P2) from the data in Tables 5 and 6. FIG. 5 shows a graphic comparison of the degradant methyleneglycol fluoromethyl hexafluoroisopropyl ether (S1) as it appears in Examples 5 and 6. Both FIG. 4 and FIG. 5 demonstrate that the degradation of sevoflurane is inhibited by the addition of water at 400 ppm.

EXAMPLE 7

Additional Studies of Sevoflurane Degradation in Activated Type III Amber Glass Bottles Sevoflurane was decanted from the five bottles of the Study Sevo Group from Example 6. Each bottle was rinsed thoroughly with fresh sevoflurane. Approximately 125 mL of water-saturated sevoflurane was then put into each bottle. The five bottles were then placed on a mechanical roller for approximately two hours to allow the water to coat the activated glass surfaces. The water-saturated sevoflurane was then drained form each bottle and replaced by 100 mL of sevoflurane containing 400 (spiked) ppm of water. Gas chromatography analysis for all samples was performed after heating at 50° C. for 18 hours, 36 hours, and 178 hours. Bishexafluoroisopropyl ether (P2) and total degradants were measured. The results are shown below in Table 7.

TABLE 7

| | Degradation Products (ppm) | | | | | |
|---|---|---|---|---|---|---|
| | HFIP | | P2 | | Total Degradants | |
| Time | 36 hour | 178 hour | 36 hour | 178 hour | 36 hour | 178 hour |
| Study Group (400 ppm water) | | | | | | |
| 1 | <10 | 16 | <10 | <10 | <50 | <50 |
| 4 | <10 | <10 | <10 | <10 | <50 | <50 |
| 6 | <10 | 28 | <10 | <10 | <50 | <50 |
| 9 | <10 | 15 | <10 | <10 | <50 | <50 |
| 10 | <10 | 19 | <10 | <10 | <50 | <50 |

The results in Table 7 demonstrate that the degradation of sevoflurane was greatly inhibited by treating the activated glass surface with water saturated-sevoflurane prior to heating.

What is claimed is:

1. An anesthetic composition comprising a quantity of sevoflurane and a Lewis acid inhibitor, the Lewis acid inhibitor being present in an amount of at least 150 parts per million parts of the anesthetic composition.

2. The composition of claim 1 wherein the Lewis acid inhibitor is water.

3. The composition of claim 2 containing at least about 0.04% w/w to about 0.14% w/w of water.

4. A method of preparing the anesthetic composition of claim 1 comprising the step of adding the Lewis acid inhibitor to the quantity of sevoflurane.

5. A method of preparing the anesthetic composition of claim 1 comprising the step of adding the quantity of sevoflurane to the Lewis acid inhibitor.

6. A method of preventing degradation by Lewis acids of a quantity of sevoflurane, the method comprising providing a quantity of sevoflurane, and adding to the quantity of sevoflurane an amount of a Lewis acid inhibitor, the amount of the Lewis acid inhibitor being selected such that the Lewis acid inhibitor is present in an amount of at least 150 parts per million parts of a resulting combination of the quantity of sevoflurane and the amount of the Lewis acid.

7. The method of claim 6 wherein the Lewis acid inhibitor is selected from a group consisting of water, butylated hydroxytoluene, methylparaben, propylparaben, propofol and thymol.

8. The method of claim 6 wherein the Lewis acid inhibitor is water.

9. An anesthetic composition comprising a quantity of sevoflurane and an amount of water, the amount of water selected such that water is present in an amount of at least 150 parts per million parts of the anesthetic composition.

10. A method of preventing degradation by Lewis acids of a quantity of sevoflurane, the method comprising:
   providing a quantity of sevoflurane; and
   adding to the quantity of sevoflurane an amount of water, the amount of water being selected such that water is present in an amount of at least 150 parts per million parts of a resulting combination of the quantity of sevoflurane and the amount of water.

* * * * *